United States Patent
Raulerson et al.

(10) Patent No.: US 6,551,281 B1
(45) Date of Patent: Apr. 22, 2003

(54) GUIDE WIRE ADVANCER AND ASSEMBLY AND METHOD FOR ADVANCING A GUIDE WIRE

(75) Inventors: J. Daniel Raulerson, Brewton, AL (US); Timothy Schweikert, Levittown, PA (US)

(73) Assignee: Medical Components, Inc., Harleysville, PA (US)

(*) Notice: Subject to any disclaimer, the term of this patent is extended or adjusted under 35 U.S.C. 154(b) by 0 days.

(21) Appl. No.: 09/482,454

(22) Filed: Jan. 13, 2000

(51) Int. Cl.$^7$ ............................................. A61M 5/178

(52) U.S. Cl. ................................................. 604/164.13

(58) Field of Search ..................... 604/164.01, 164.06, 604/164.07, 164.08, 164.11, 164.12, 164.13, 264, 272, 523, 528, 533; 606/108

(56) References Cited

U.S. PATENT DOCUMENTS

| | | |
|---|---|---|
| 3,416,531 A | 12/1968 | Edwards |
| 3,521,087 A | 7/1970 | Lombardi |
| 3,521,620 A | 7/1970 | Cook |
| 3,547,103 A | 12/1970 | Cook |
| 3,561,445 A | 2/1971 | Katerndahl et al. |
| 3,774,605 A | 11/1973 | Jewett |
| 3,826,256 A | 7/1974 | Smith |
| 3,835,854 A | 9/1974 | Jewett |
| 3,847,140 A | 11/1974 | Ayella |
| 3,995,628 A | 12/1976 | Gula et al. |
| 4,003,369 A | 1/1977 | Heilman et al. |

(List continued on next page.)

FOREIGN PATENT DOCUMENTS

RU        207358        11/1965

OTHER PUBLICATIONS

Arrow International, Inc. "Arrow AK–04225 CVC Kit" Brochure (1986).
Blitt, et al., "External Jugular Vein approach: J–Wire Technique" (1974), pp. 118–120.
Casey D. Blitt, et al. "Central Venous Catheterization Via the External Jugular Vein—A Technique Employing The J–Wire", *JAMA*, vol. 229, Bo. 7, pp. 817–818 (1974).
Sven Ivar Seldinger, "Catheter Replacement of the Needle In Percutaneous Arteriography", pp. 368–376 (1953).

*Primary Examiner*—Manuel Mendez
*Assistant Examiner*—Mark Han
(74) *Attorney, Agent, or Firm*—Woodcock Washburn LLP (57) ABSTRACT

An advancer for advancing a guide wire includes a distal portion having a passageway extending longitudinally therethrough. The distal portion is capable of straightening the guide wire. The advancer further includes a proximal portion having a passageway extending longitudinally therethrough and a central portion having first and second curved surface members which extend between the distal portion and the proximal portion. The curved surface members define an opening therebetween to provide access for a user's thumb and finger to advance a guide wire through the advancer. Also disclosed is a guide wire advancer assembly which includes the advancer and a guide wire storage tube. The tube has an outer diameter which is substantially the same as an inner diameter of the proximal portion and which has the guide wire enclosed within the storage tube. A method for straightening a guide wire for insertion into a patient includes the steps of inserting a tip of the guide wire advancer into a proximal end of a guide wire introducer. The end of the guide wire is passed through the proximal end of the guide wire advancer, and the guide wire is advanced through the guide wire advancer such that it passes through the opening in the tip of the guide wire advancer and into the opening in the guide wire introducer. The guide wire is then passed through the guide wire introducer and into the patient.

17 Claims, 5 Drawing Sheets

U.S. PATENT DOCUMENTS

| | | |
|---|---|---|
| 4,080,706 A | 3/1978 | Heilman et al. |
| 4,160,451 A | 7/1979 | Chittenden |
| 4,274,408 A | 6/1981 | Nimrod |
| 4,342,313 A | 8/1982 | Chittenden |
| 4,397,091 A | 8/1983 | Gustavsson et al. |
| 4,417,886 A | 11/1983 | Frankhouser et al. |
| 4,425,908 A | 1/1984 | Simon |
| 4,534,363 A | 8/1985 | Gold |
| 4,641,649 A | 2/1987 | Walinsky et al. |
| 4,650,472 A | 3/1987 | Bates |
| 4,676,249 A | 6/1987 | Arenas et al. |
| 4,724,846 A | 2/1988 | Evans |
| 4,726,369 A | 2/1988 | Mar |
| 4,799,496 A | 1/1989 | Hargreaves et al. |
| 4,813,938 A | 3/1989 | Raulerson |
| 4,844,092 A | 7/1989 | Rydell et al. |
| 4,860,757 A | 8/1989 | Lynch et al. |
| 4,917,094 A | 4/1990 | Lynch et al. |
| 5,045,065 A | 9/1991 | Raulserson |
| 5,125,905 A | 6/1992 | Wright et al. |
| 5,125,906 A | 6/1992 | Fleck |
| 5,186,179 A | 2/1993 | MacEachern |
| 5,263,938 A * | 11/1993 | Orr et al. .................. 604/171 |
| 5,273,042 A | 12/1993 | Lynch et al. |
| 5,366,444 A | 11/1994 | Martin |
| 5,438,993 A | 8/1995 | Lynch et al. |
| 5,448,993 A | 9/1995 | Lynch et al. |
| 5,484,419 A | 1/1996 | Fleck |
| 5,507,300 A | 4/1996 | Mukai et al. |
| 5,810,012 A | 9/1998 | Lynch et al. |

\* cited by examiner

GUIDE WIRE ADVANCER AND ASSEMBLY AND METHOD FOR ADVANCING A GUIDE WIRE

BACKGROUND OF THE INVENTION

Catheters may be used for introducing and removing fluids in and from various vessels and cavities throughout the body. Central venous catheters, for example, are generally placed in four common locations within the chest and/or in the femoral vessels. They may be placed, for example, in either the right or left subclavian vein or in the right or left internal jugular vein. Such catheters are largely introduced in accordance with the known Seldinger technique, which involves use of a guide wire to properly place the catheter in the catheterized area.

Using landmarks, vessels are identified and may be cannulated by first aspirating the vessel with a long hollow needle, which may be attached to a syringe or other aspirating device to ensure that the vessel has been properly located. When the vessel has been properly located and aspirated, if a syringe is used, the syringe is disconnected and a thin guide wire is passed through the needle into the hollow passage, or lumen, of the vessel. Other introducers allow the guide wire to pass through the syringe or device without removing the device from the needle. The needle or other introducer device is then removed, leaving one end of the guide wire within the vessel. The other end of the guide wire projects beyond the surface of the skin.

At this point, the simplest method of catheter placement is to pass a catheter into the vessel directly over the guide wire. The guide wire is then removed, leaving the catheter in position within the vessel. The catheter as placed can then function in various applications such as infusion, perfusion, hemodialysis and the like.

The guide wires used for such procedures are generally spring wires which typically have a curved J-shaped tip. The nature of the spring wire, which is typically constructed from a memory alloy, causes the tip to return to the J-shape after applied stress is removed. Therefore, in order to slide the tip through the device and to keep the wire from bending back on itself while entering the patient, such wires are typically introduced through a straightening device. The guide wire has a relatively long length. For convenience, the wire is typically packaged and used as a coil. The coils generally have plastic clips which help to hold the coil together for handling. In addition, the coils can be packaged in protective storage tubes which also may use clips to hold the tubes in a coiled configuration.

The primary cost incurred in preparing catheter and catheter introducer kits are the catheters, wires and needles. Other accessories and components which facilitate catheter introduction are also included in such kits. However, in preparing such kits, manufacturers must balance the objectives of making such kits as easy to use and as complete as possible for medical personnel against the objective of providing a commercially acceptable cost for such kits. One method of minimizing overall cost is to minimize the cost of the accessory items. The kits typically include a catheter, a guide wire, a guide wire straightener and/or feeding mechanism, an introducer and/or needle, a scalpel, connectors and various other related instruments for introducing the catheter into a patient. In addition, the accessory items may be packaged alone as an introducer kit which is sold separately from an individual catheter, or as a combined catheter and introducer kit which includes a specific catheter and its associated accessories. As such, there is a need in the art to provide accessories which are cost effective to manufacture and which do not significantly increase the cost of the kit, but which are effective in facilitating insertion of the guide wire and catheter.

As discussed further below, there are various devices available for advancing a guide wire through an introducer, such as a needle, into a patient. However, there is an on-going need in the art to improve upon such guide wire advancers with the objective of reducing their cost of manufacture to reduce the overall cost of introducer and catheter kits, while maintaining and/or improving their effectiveness in advancing a guide wire into a patient as well as making them easier to use and manipulate as discussed below.

In addition to the manufacturing cost objective noted above, the mechanical difficulties encountered by a physician or other medical personnel using such guide wires typically are the result of the need to use two hands to handle the guide wire and to operate an advancing apparatus while inserting the guide wire through the needle into the patient. Various prior art devices are directed to simplifying the advancing and insertion procedure, including a plastic cone having a hole at the tip of the cone for passing the guide wire through the hole into the introducer hub, and a shuttling device as described in U.S. Pat. No. 4,713,059. These devices, while assisting in advancing the wire through the introducer and guiding the wire into the needle, require two hands to operate.

Syringes have been adapted which advance and straighten the wire and pass the wire through the syringe directly into the needle without detaching the syringe. While such devices minimize bleeding, they are highly specialized and complex with respect to the central passages and valves within the syringe, and occasionally, difficulty is still encountered in feeding the guide wire into the end of the syringe, requiring a peripheral straightening device. Due to the more complex nature of such syringes, while they may improve effectiveness in handling the guide wire, they are relatively expensive to manufacture. Examples of guide wire introducing syringes may be found in U.S. Pat. Nos. 4,274,408, 4,417,886, 4,813,938, and 5,045,065.

Other solutions to the problem of two-handed guide wire advancing and straightening include a device as described in U.S. Pat. No. 5,125,906, which teaches a trigger-like handle with a clip which can be attached to a guide wire feeding tube or coil. The device has a frustoconical, tapered, distal end portion. The device is held with the fingers coiled around the trigger handle and the guide wire is fed into the device through a proximal opening, slid across a flat surface by the thumb and through the distal end portion into a syringe or needle introducer. A modified version of the device is disclosed in U.S. Pat. No. 5,484,419, which includes an additional, separate conical end fitting which can be placed over the end portion to help feed the guide wire into the needle and which has an arched underneath surface for facilitating handling of the device to enhance sliding of the guide wire over a flat top surface of the device.

A virtually identical device is described in U.S. Pat. No. 5,507,300, which provides a rubber band along the wire guide to allow the physician to stop the insertion of the guide wire without letting the guide wire slip along the guide.

U.S. Pat. No. 5,366,444 discloses a guide wire advancer which provides a head with a guide opening, a discharge opening, and an open platform therebetween. A guide wire is advanced over the platform with a thumb, with a forefinger engaging a depression on an underside of the platform.

Other devices disclosed by U.S. Pat. Nos. 4,860,757, 4,917,094, 5,273,042, 5,438,993, and 5,448,993 describe a guide wire housed in a tube with apertures or a conical straightener as described above with a thumb opening cut into the conical portion. A physician's thumb fits into the aperture to engage the guide wire to advance or retract the guide wire through the tube.

The above-described guide wire straighteners assert one-handed operation of the device to introduce the guide wire into the needle. However, problems may still be encountered in holding the tip of the straightening or advancing device firmly within the needle fitting while introducing the guide wire into the needle to avoid slipping of the device out of the needle while advancing the guide wire across the device with the physician's thumb. Further, the physician is generally wearing rubber gloves, which reduce the tactile sensation of the thumb as the thumb operates the guide wire. In addition, it would be advantageous to further reduce the cost of making such guide wire advancing devices and thereby reduce the overall cost of introducer kits and catheter kits which include the straightener and feeding devices and other accessories.

Therefore, there is a need in the art for a guide wire advancer and/or straightening device which is cost effective to manufacture and which minimizes the overall cost of introducer kits and catheter kits incorporating the device. There is also a need for such a device which is easy to operate with only one hand, which does not slip from the needle fitting during the guide wire advancing procedure such that additional stability in handling can be achieved and which provides greater tactile feel to the user for controlling the rate of advancement of the wire into the patient. There is further a need in the art for such an advancing device which advances easily into a guide wire feeding tube while still firmly gripping the tube once inserted. The present invention satisfies such needs.

BRIEF SUMMARY OF THE INVENTION

In one aspect, the present invention is a guide wire advancer which comprises a distal portion having a passageway extending longitudinally therethrough, the distal portion being capable of straightening a guide wire; a proximal portion having a passageway extending longitudinally therethrough; and a central portion having first and second members which extend between the distal portion and the proximal portion. The first and second members define an opening therebetween to provide access for a user's thumb and finger to advance the guide wire through the advancer.

In another aspect, the present invention is a guide wire advancer assembly which comprises a guide wire assembly comprising a distal portion having a passageway extending longitudinally therethrough, and which is capable of straightening a guide wire; a proximal portion having a passageway extending longitudinally therethrough; a central portion having first and second members which extend between the distal portion and the proximal portion, the first and second members defining an opening therebetween to provide access for a user's thumb and finger to advance the guide wire through the advancer; and a guide wire storage tube having an outer diameter being substantially the same as an inner diameter of the proximal portion.

Also includes in the invention is a method for using an advancer. The advancer in the method comprises a distal portion having a passageway extending longitudinally therethrough and having an exterior surface; a proximal portion having a passageway extending longitudinally therethrough; and a central portion having first and second members extending between the distal portion and the proximal portion. The first and second members define an opening capable of providing access for a user's thumb and finger. The method comprises the steps of inserting a distal portion of the advancer into a proximal end of a guide wire introducer; passing an end of the guide wire through the proximal portion of the advancer; and feeding the guide wire through the advancer using a thumb and a finger in the opening in the central portion such that the end of the guide wire passes through the passageway in the distal portion of the advancer, through the guide wire introducer, and into a patient.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown. In the drawings, like numerals are used to indicate like elements throughout. In the drawings.

DETAILED DESCRIPTION OF THE INVENTION

Certain terminology is used in the following description for convenience only and is not limiting. The words "lower" and "upper" and "top" and "bottom" designate directions in the drawings to which reference is made. The words "distal" and "proximal" respectively designate directions in the drawings toward and away from the insertion end of the device. The terminology includes the words above specifically mentioned, derivatives thereof and words of similar import.

Figure 1:
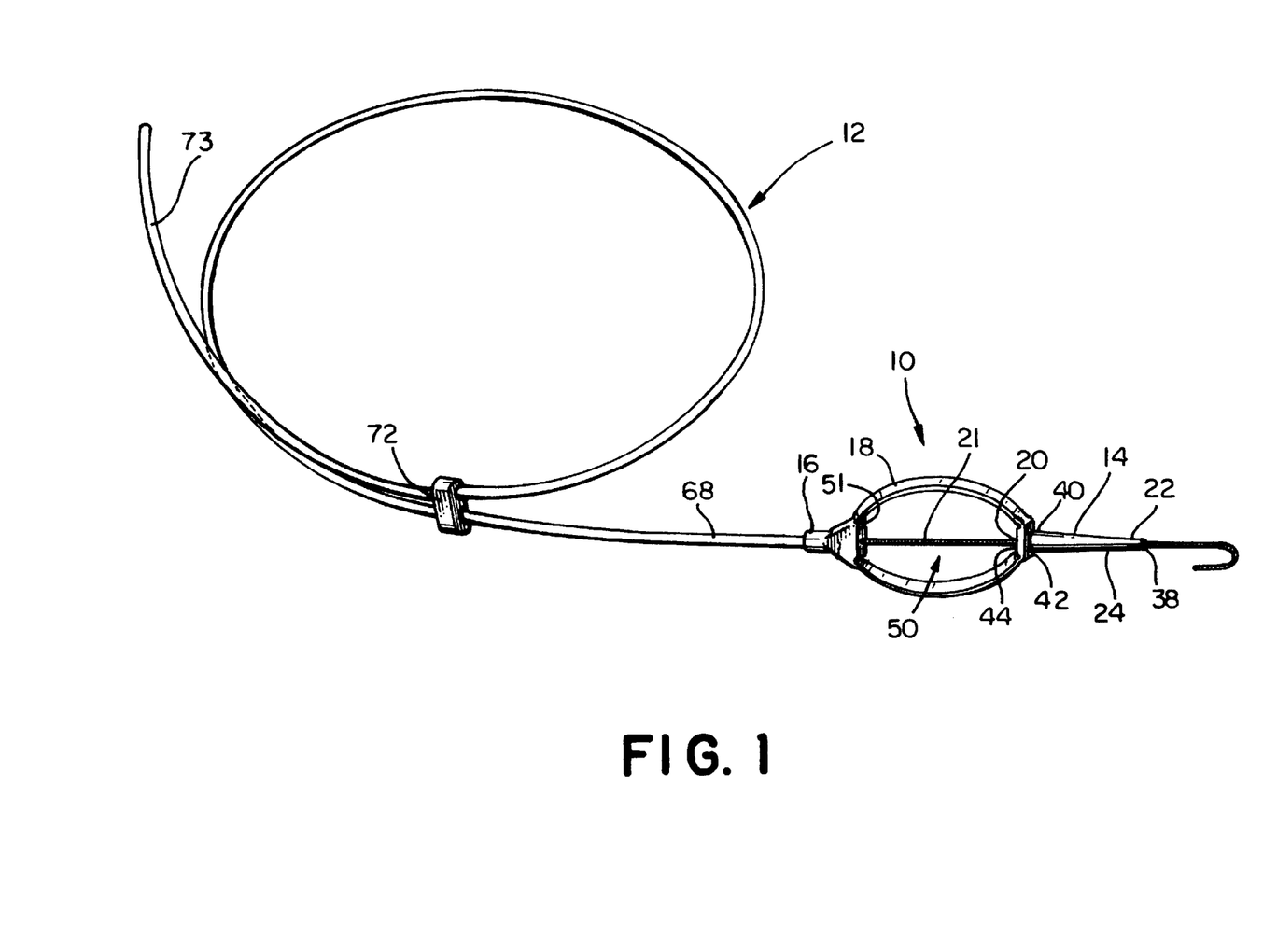
FIG. 1 is a perspective view of a guide wire advancer assembly in accordance with the present invention.
Figure 2:
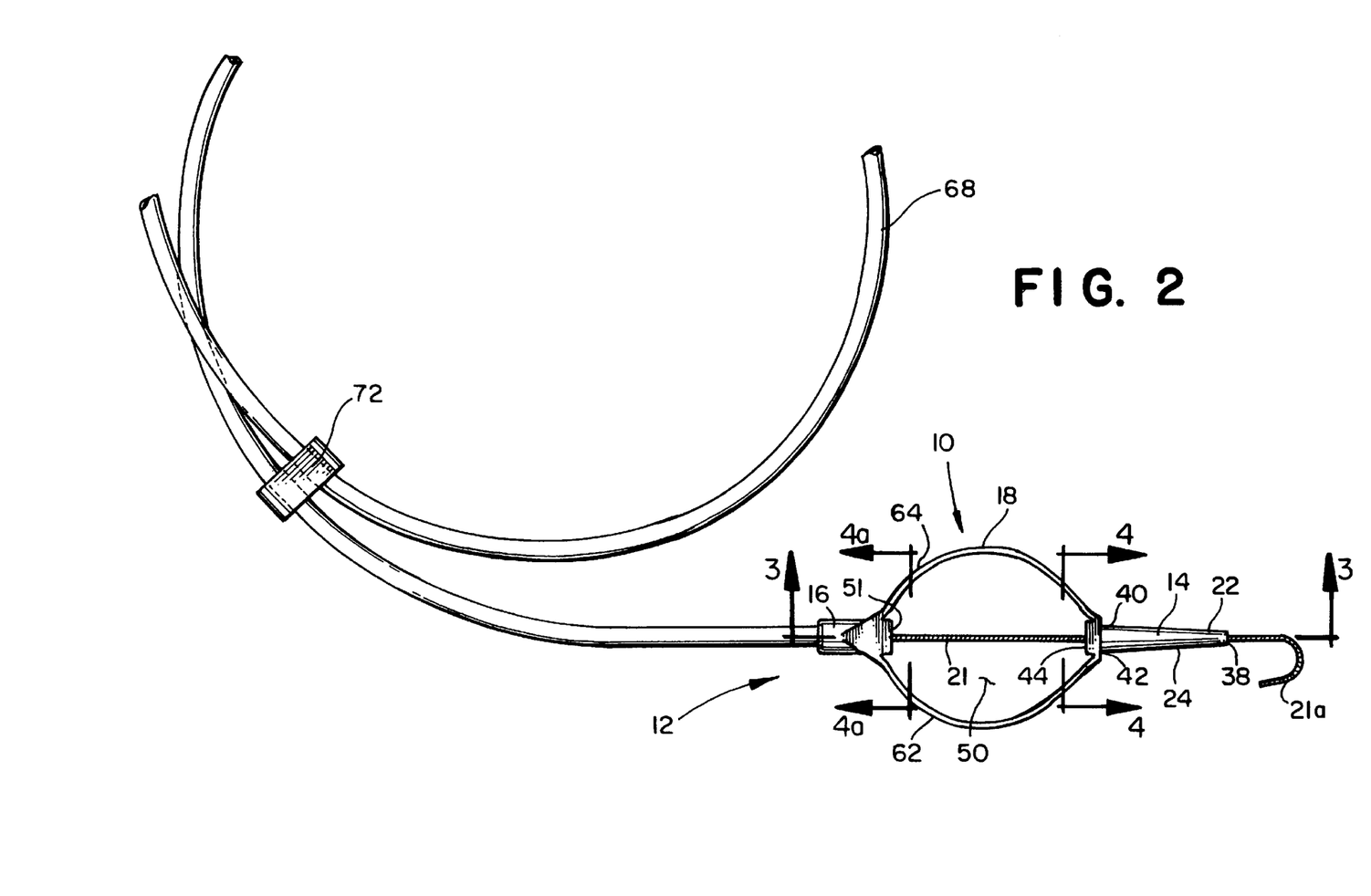
FIG. 2 is a plan view of the guide wire advancer assembly of FIG. 1.
Figure 3:
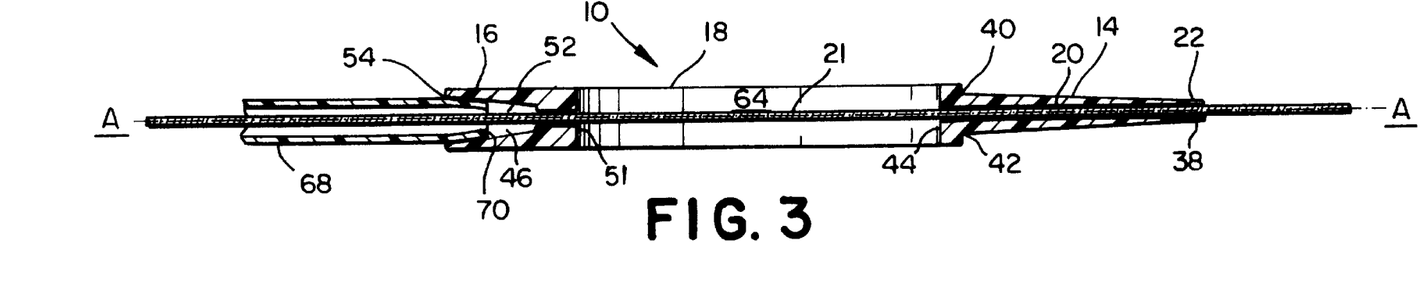
FIG. 3 is a cross-sectional view of the guide wire advancer assembly taken along line 3—3 of FIG. 2.
Figure 4:
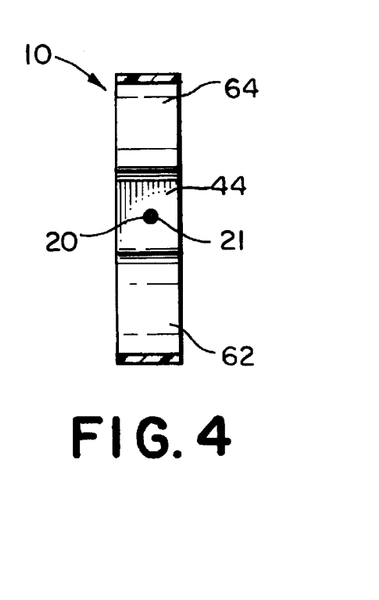
FIG. 4 is a cross-sectional view of the advancer taken along line 4—4 of FIG. 2.
Figure 4A:
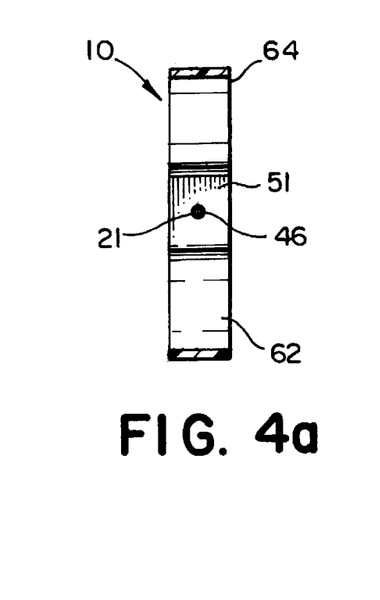
FIG. 4a is a cross-sectional view of the advancer taken along line 4a—4a of FIG. 2.
Figure 5:
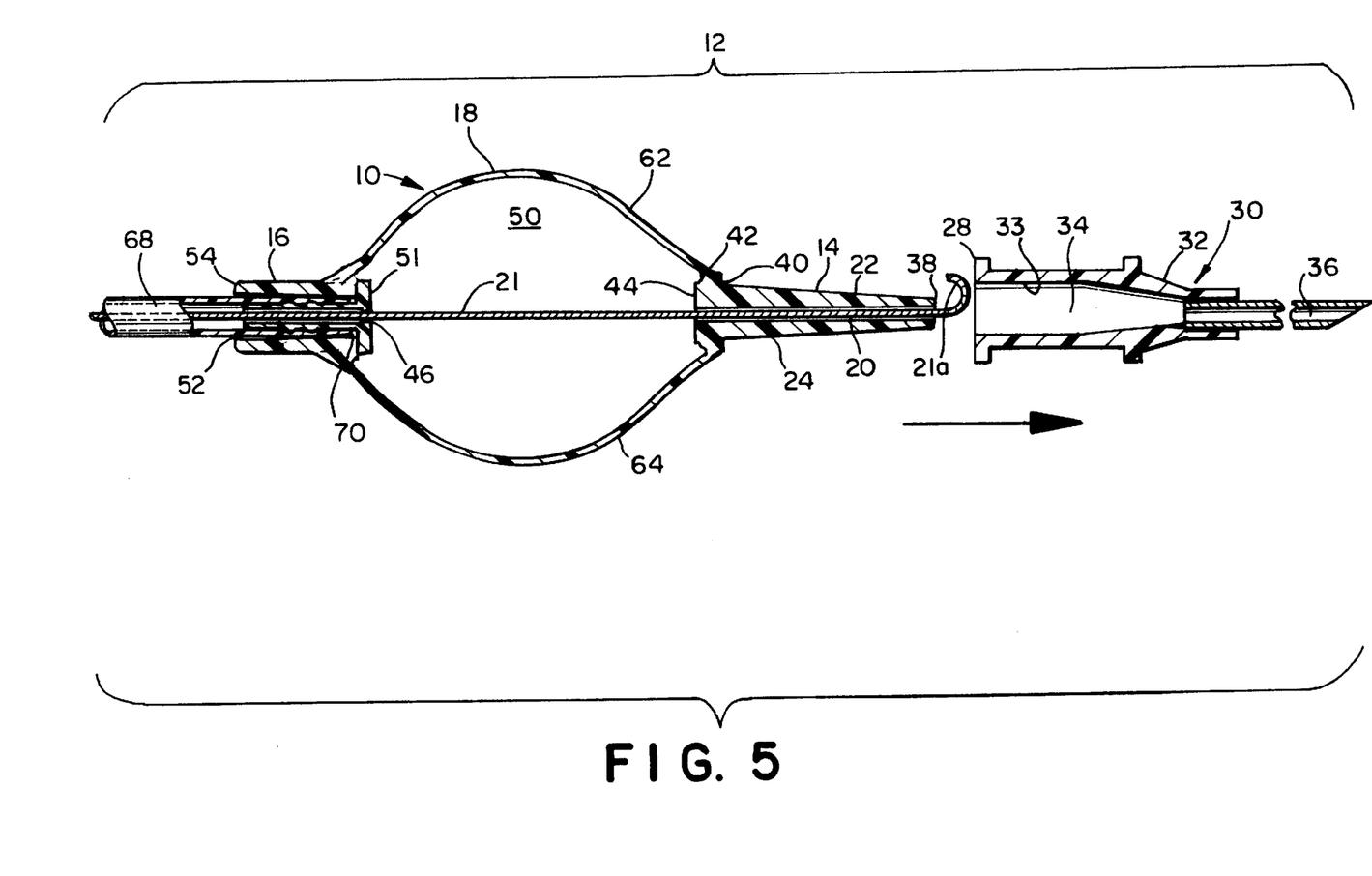
FIG. 5 is a partially broken cross sectional view of the guide wire advancer assembly of FIG. 1 prior to being inserted into an introducer needle.
Figure 6:
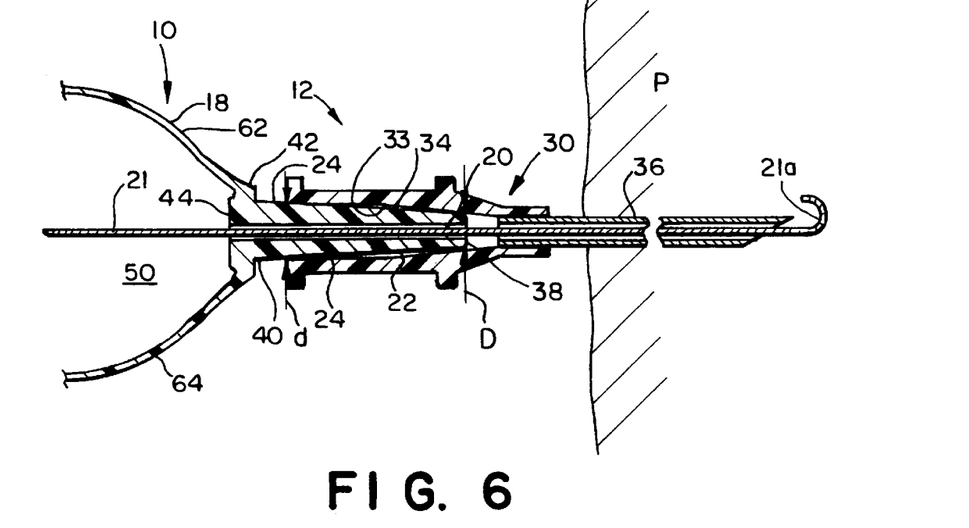
FIG. 6 is an enlarged, partially broken cross sectional view of a portion of the advancer assembly of FIG. 1 inserted into an introducer needle which has be inserted into a patient.

Referring now to the drawings in detail, there is shown in FIGS. 1–7 a guide wire advancer assembly, generally designated as 12, and a guide wire advancer, generally designated as 10, according to one preferred embodiment of the present invention. The advancer 10 has a distal portion 14, a proximal portion 16 and a central portion 18 located between the distal and proximal portions 14, 16. A longitudinal direction of the advancer 10 is referenced by a central longitudinal axis A—A as shown in FIG. 3. As best shown in FIG. 3, the distal portion 14 has a passageway 20 which extends longitudinally therethrough, preferably along the longitudinal axis A—A. The diameter of the passageway 20 is preferably sized to receive a guide wire 21 therein as shown in FIGS. 5 and 6. Preferably, for different gauge guide wires, the diameter of the passageway 20 and the associated advancer 10 can be larger or smaller with respect to the size of the guide wire 21 to be used. The diameter of the passageway 20 should be sized such that the guide wire 21 fits through snugly, with minimal clearance between the outer diameter of the guide wire 21 and the diameter of the passageway 20 of the distal portion 14, but not so tightly as to inhibit advancement of the guide wire 21 through the passageway 20. Preferably, the guide wire 21 should substantially fill a lumen 36, as shown in FIG. 6, to minimize blood loss through a separate introducer such as a device 30 (not part of the present invention) as shown in FIGS. 5 and 6, but should still be able to be advanced smoothly through the passageway 20, into the introducer device 30 and into a patient "P" (shown in FIG. 6) without too much effort on the part of the physician or other medical personnel using the device 10.

The introducer used can vary and many are known in the art. The introducer may be a conventional introducer or the advancer may be used to feed directly into a catheter and/or catheter fitting which can itself serve as an introducer. As such, "introducer" as used herein includes any intervening device between the advancer 10 and the patient's vessel or cavity for receiving the guide wire 21. For example, the introducer device 30 may be a needle having a proximal coupling or other fitting which remains distally inserted in a patient after disconnect of an aspirating syringe, or an apparatus such as a catheter introducer syringe which has a needle end inserted in the patient and a syringe body or other proximal attachment connected to the needle. When such syringes, or similar devices, are used as the introducer, the proximal opening for inserting the tip 22 would generally be located on the proximal end of the syringe body or other proximal needle attachment. If the introducer device 30 is a needle, the opening for inserting the tip 22 would be the coupling or other proximal end fitting on the needle after the aspirating syringe has been removed.

The wire 21 should advance through with an easy advancing motion, but should not interfere with the physician feeling any obstruction within the patient during the feeding operation as described further below. Preferably, some tactile control between the wire 21 and the physician's thumb and forefinger is preferred. A preferred clearance between the outer diameter of the guide wire 21 and the diameter of the passageway 20 is sufficient to allow free passage of the guide wire 21 through the passageway 20. Preferably, a distal tip 21a of the guide wire 21 is curved as shown in FIGS. 1, 2, 5, and 6. The tip is curved to prevent the tip 21a from catching and perforating the vessel as the guide wire 21 is being passed through the lumen of a vessel in the patient P.

Referring to FIGS. 1, 2, 3, 5, and 6, the distal portion 14 of the advancer terminates in a tip 22 which may have any suitable shape. Preferably, the distal portion 14 is configured to fit within a fitting on the proximal end of an introducer such as the introducer 30 as described further below. The distal portion 14, and more specifically, the tip 22, is preferably conical, but may be also be cylindrical along its length or cylindrical along only a portion of its length with a graduated shape such as a smaller diameter cylindrical portion or an end portion which is tapered or conical. Preferably, the tip 22 of the distal portion 14 tapers down from a proximal end 40 to a distal end 38. A bullet-shaped end may also be used wherein the cross-section in the longitudinal direction would appear parabolic. The shape may vary, however, it is preferred that the tip 22 mates with the type of introducer selected. The actual shape of the tip 22 should be determined by a number of factors, including but not limited to, ease of insertion and the shape of the passageway through a fitting into a proximal end of an introducer into which the tip 22 is to be inserted.

The tip 22 further has an exterior surface 24 which may be smooth or rough. While not preferred, longitudinally extending gripping ribs (not shown) can be provided to extend along the surface 24 of the tip 22, particularly if the tip is cylindrically shaped, or along a portion of the surface 24 of the tip 22. The exterior surface 24 of the tip 22 is preferably adapted to mate with an interior surface 33 of an introducer. For example, if a passageway 34 in the proximal end 28 of the introducer 30 were conically shaped, the exterior surface 24 of the tip 22 may be conically configured to more smoothly enter the passageway 34 and to mate more securely with the interior surface 33 of the introducer 30 as shown in FIGS. 5 and 6.

FIGS. 5 and 6 show a preferred embodiment of the advancer 10 being inserted in the proximal end 28 of the introducer device 30. The introducer device 30 generally includes a Luer lock connector 32 which has been disconnected from a mating fitting on an aspirating syringe (not shown). A connector passageway 34 is in fluid communication with a lumen 36 extending through the introducer device 30. The lumen 36 is typically inserted into a vessel such as a blood vessel (not shown) and would be in open communication with the vessel. The tip 22 as shown in FIGS. 5 and 6 is generally conical and has an outer diameter "D" at the most distal end 38 of the tip 22 which is smaller than the maximum internal diameter "d" of the passageway 34 of the connector 32. The tip 22 preferably has an outer diameter D at the proximal end 40 of the tip 22 which is larger than the maximum inner diameter d of the passageway 34 of the connector 32. As a result, the distal end of the tip 22 would slide within the passageway 34 until the point at which the tip 22 no longer fits within the passageway 34 as shown in FIG. 6. At this point, the exterior surface 24 will engage the interior surface 33 of the proximal end 28 of the introducer 30. The exterior surface 24, once inserted in the proximal end of the introducer 30, will engage the interior surface 33 of the proximal end of the introducer 30 such that the advancer 10 will be more stable and more easily held in place and manipulated, thereby minimizing problems associated with slippage of prior art straightening devices from introducers. Alternatively, although not preferred, the outer diameter D can be smaller than the inner diameter d such that the entire tip 22 can be inserted into the passageway 34. Those skilled in the art will realize that other similar tips can be made with other tip configurations, as described above, without departing from the spirit and scope of this invention. For example, the other tip configurations can include ribs, gripping surfaces and other types of surfaces.

The guide wire introducer 30 may be any of the introducers described above, and the method will be exemplified as shown in FIGS. 5 and 6 by the introducer 30 in the form of a needle having a fitting such as the connector 32 at its proximal end 28 which has an opening such as the passageway 34 through the connector 32. The opening 34 should be in alignment with the distal end 38 of the tip 22 of the advancer 10. As shown in FIGS. 5 and 6, the passageway 20 in the tip 22 having the guide wire 21 inserted therein is in alignment with the passageway 34 through the connector 32.

The passageway 34 is in communication with the lumen 36 through the introducer 30.

In the embodiment of the advancer 10 of FIGS. 1–6, the distal portion 14 preferably has a rectangularly shaped portion 42 attached to the proximal end 40 of the tip 22. The rectangularly shaped portion 42, as well as the entire advancer 10, is preferably integrally molded as one piece. The rectangularly shaped portion 42 preferably extends transversely across the advancer 10 and has an inner surface 44 which faces the central portion 18. The passageway 20 terminates at the surface 44. When passing the guide wire 21 through the advancer 10 in a direction from the proximal portion 16 to the distal portion 14, the guide wire 21 would enter the distal portion 14 through the terminal end of the passageway 20 at the surface 44.

Referring to FIGS. 3 and 5, the proximal portion 16 of the advancer 10, has a passage 46 which extends longitudinally through the proximal portion 16 as shown in FIGS. 3 and 5 and which is sized to receive the guide wire 21 to facilitate insertion of the guide wire 21 through the advancer 10. In the embodiment shown, the passage 46 is axially aligned with the passageway 20 through the distal portion 14, generally along the central longitudinal axis A—A. While such alignment is not necessary for the invention, it is preferred for ease of manufacture and to facilitate advancing of the guide wire 21 through the advancer 10. The proximal portion 16 preferably has an inner end surface 51, shown in FIG. 4a, which faces, but is spaced from, the inner surface 44 of the distal portion 14.

The proximal portion 16 preferably includes an interior surface 52 which preferably tapers inwardly from a proximal end 54 to the end surface 51 through the passageway 46 to facilitate insertion of the guide wire 21 from the proximal end 54. The proximal end 54 as shown in FIGS. 3 and 5 is configured to fit over an open end of a typical guide wire storage tube 68 and to engage the storage tube 68 with an interference fit so that the storage tube 68 will not slip from the proximal end 54. However, the fit between the storage tube 68 and the proximal end 54 should be loose enough to allow the storage tube 68 to easily rotate about the axis A—A, allowing the plane of the storage tube 68, as shown by the plane of the paper in FIG. 2, to rotate to facilitate handling by the physician during use. The opening of the proximal end 54 may be varied for different sized tubes 68.

The central portion 18 of the advancer 10 includes a pair of first and second longitudinally extending, preferably curved connecting members 62, 64 which interconnect the distal and proximal portions 14, 16. Preferably, the connecting members 62,64 are flexible, for reasons that will be explained. The central portion 18 may be transversely spaced from and on opposing sides of the passageways 20, 46 through the distal and proximal portions 14, 16, respectively, and extend between the distal portion 14 and the proximal portion 16. Each connecting member 62, 64 is preferably generally arcuate such that an interior curved surface of each connecting member 62, 64 faces the central longitudinal axis A—A. However, other shapes besides arcuate are envisioned and may be used within the scope of the invention. Such other shapes can include polygonal such as quadrilateral, hexagonal, octagonal as well as others not mentioned herein. The central portion 18 includes an opening 50 defined by a space between the curved surfaces of the connecting members 62, 64 for advancing the guide wire 21 through the advancer 10.

Figure 7:
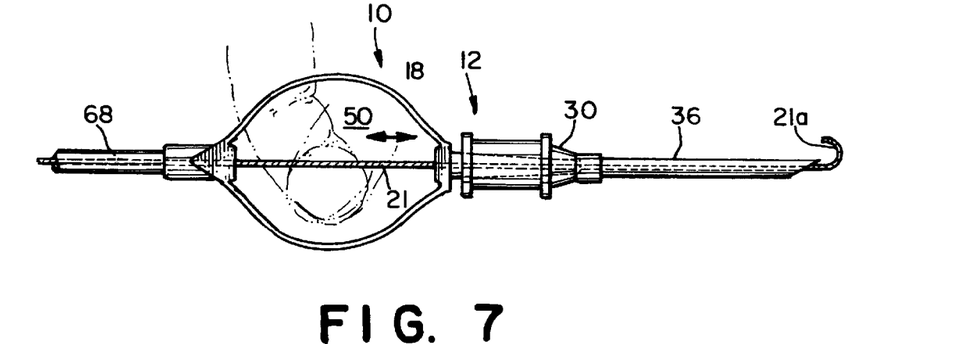
FIG. 7 is a perspective view showing a user manipulate a guide wire using the guide wire advancer assembly.

The opening 50 preferably provides access for the user to manipulate and advance the guide wire 21, preferably by gripping the wire 21 between a thumb and forefinger as shown in FIG. 7 and feeding the wire 21 in a controllable manner. It is important is that the opening 50 between the members 62, 64 be configured to be sufficiently large so as to provide access to the physician to grip the guide wire 21 with the thumb and forefinger through the opening 50 at the central portion 18 to advance the guide wire 21 through the advancer 10. Unlike other thumb sliding advancers, the present invention allows the user to grip and pinch the wire 21 and feed it at the physician's desired speed into the patient, starting and stopping controllably without slipping of the thumb or the guide wire 21.

In the preferred embodiment, the invention further includes an assembly 12 for feeding and straightening a guide wire 21 as shown in FIG. 1. The assembly 12 includes the advancer 10 connected to the guide wire storage tube 68. The guide wire 21 is enclosed within the storage tube 68, and the storage tube 68 can easily be held in place while the guide,wire 21 is advanced forward toward the central portion 18. The storage tube 68 is preferably a flexible plastic tube which may be formed of any suitable polymeric material. Such tubes are well known in the art and are commercially available. The tube 68 has an open distal end 70 which connects to the proximal portion 16 of the advancer 10, preferably by coupling with the interior surface 52. The open distal end 70 slides within the interior surface 52 and preferably tightly, and more preferably interferingly, fits within the passageway 46 in the proximal portion 16 such that the storage tube 68 will not easily fall off of the proximal portion 16 of the advancer 10. The storage tube 68 may have one or more securing clips 72 which are typically sold with packaged storage tube coils. Such securing clips 72 help to retain the storage tube 68 in a coiled condition as seen in FIGS. 1 and 2. The guide wire 21 extends longitudinally, and preferably loosely, within the storage tube 68. The proximal end 73 of the storage tube 68 may be equipped with couplings or a sealing cap (not shown) for preventing the guide wire 21 from advancing in the proximal direction out the proximal end 73 of the storage tube 68. While a storage tube 68 is preferred, a bare coil of guide wire 21 may also be inserted directly into the proximal portion 16 of the advancer 10 without any structure directing the wire 21 into the advancer 10. However, the guide wire storage tube 68 improves handling of the coiled guide wire 21 and helps to prevent contamination and to maintain the guide wire 21 in a sterile condition. When the guide wire 21 is fully within the advancer 10 such that the guide wire 21 extends through the distal portion 14 from the storage tube 68, the guide wire 21 preferably extends across the central portion 18 such that the guide wire 21 is generally extends along the longitudinal axis A—A.

The advancer 10 of the present invention may be made of any suitable material preferably capable of being sterilized, such as metals, metal alloys, polymeric and/or elastomeric materials. The material need not be biocompatible as the advancer 10 itself is not designed to enter the patient P. In the preferred embodiment, for manufacturing economy and simplicity, the advancer 10 is made of a heat moldable or thermoformable polymeric or elastomeric material. The preferred polymeric, materials include thermoplastic or thermosetting polymers and copolymers, and more preferably, thermoplastic polymers which are capable of being injection molded or extruded. In the preferred embodiment, the advancer 10 is formed by injection molding using a mold having the desired configuration and using a rod or other means to maintain the longitudinally extending passageways 20, 46 through the distal and proximal portions 14, 16. In the preferred embodiment, the advancer 10 is formed of polyethylene, and more preferably, polypropylene. It is also within the scope of the invention to use reinforced polymeric or elastomeric or composite materials for forming the advancer with long or short fibrous reinforcements such as glass, carbon fiber, or polymeric fibers, fillers, or metal inserts or metallic wire mesh as well as any other suitable polymeric molding reinforcement. Pigments or other coloring agents may be added to the molding polymer to provide a bright or distinctive color to the advancer 10 for good visual identification during the guide wire insertion procedure.

The dimensions of the advancer 10 should be relatively small and sized to fit easily within the user's fingers while allowing a sufficiently long and wide central portion 18 for achieving adequate gripping and feeding movement using the thumb and preferably the forefinger. The size and shape of the opening 50, within the parameters as discussed above, should allow thumb and forefinger access to and movement of the particular guide wire 21 through the advancer 10. The tip 22 can similarly be sized for fitting easily into the proximal end of the guide wire introducer 30 for directing the guide wire 21 from the advancer 10 into the patient P. Preferably, the overall length of the advancer 10 from the distal end of the tip 22 to the proximal end of the proximal portion 16 is about 69 mm.

The present invention further includes a method for advancing and straightening the guide wire 21 for insertion into the patient P, preferably using an apparatus such as the advancer assembly 12 as described above. However, those skilled in the art will realize that the advancer 10 can be used alone, without the storage tube 68. Typically, the vessel to be catheterized is located and cannulated by aspirating the vessel with the introducer 30, preferably a needle. After the vessel is aspirated, guide wire 21 is inserted into the vessel through the lumen 36 of the introducer 30.

It is preferred that the device be held along the central portion 1.8 to avoid the possibility of loosening the gripping surface 24 of the tip 22 from the guide wire introducer 30, such as a needle. The user's thumb and finger, preferably forefinger, are preferably used for the manipulation and feeding of the guide wire 21 through the central portion 18. According to one preferred method, the tip 22 of the advancer 10 is inserted into the proximal end 28 of the guide wire introducer 30, which has already been inserted into the patient P, as shown in FIG. 6. Preferably the advancer 10 or the assembly 12 having the storage tube 68 and guide wire 21 as described in detail above are used in the preferred method. The end 21a of the guide wire 21 is already extended from the distal end 14 of the advancer 10 and must be straightened out prior to being inserted into the passageway 34 of the introducer 30. Once the tip 21a is inserted into the passageway 34, the user uses his/her thumb and finger, preferably the forefinger, to grasp the wire 21 and controllably feed the wire 21. The wire 21 is thus moved through the central portion 18, and pushed through the advancer 10 into the distal portion 14 and out the distal end 38 of the tip 22 in the direction of arrow "B" in FIG. 7.

In an alternately preferred method, the user grasps the guide wire 21 and the advancer 10 in one hand, and compresses the opening 50 in the advancer 10 such that the inner end surface 51 of the proximal portion 16 is advanced toward the inner end surface 44 of the distal end portion 14. The connecting members 62, 64, because of their flexibility, easily deform to allow such movement. As the advancer 10 is compressed, the guide wire 21 is advanced into the patient. The physician then releases the guide wire 21 and the advancer 10. The guide wire 21, due to friction between the guide wire 21 and the patient, remains in place and the advancer 10, due to the flexibility of the connecting members 62, 64, returns to the uncompressed position. The physician can repeat the process until the guide wire 21 is advanced a desired length.

The guide wire 21 passes from the distal end 38 in the tip 22 of the advancer 10 and into the passageway. 34 in the guide wire introducer 30. The guide wire end 21a then passes out the end of the needle 30. The needle 30 is typically already within a vessel or other area to be catheterized in a patient (not shown) which will further hold the end 21a of the guide wire 21 straight when the end 21a of the guide wire 21 passes distally out of the needle 30. Therefore, when the end 21a of the guide wire 21 passes through the distal end of the needle 30, the end 21a is still straight and may pass directly into the patient in the area to be catheterized such as a blood vessel, a body cavity, or other area to be catheterized. The introducer area keeps the tip 21a of the guide wire 21 straight until the tip 21a exits the distal end of the introducer 30 in the patient's body where the tip 21a can curl back to its natural, curved position.

Once the guide wire 21 is properly located within the patient, the storage tube 68, the advancer 10, the needle 30 or other introducer may each be removed from the proximal end of the guide wire 21. The introducer may in some cases be left on depending upon the procedure. The guide wire 21 is left in the patient with the distal end 21a in the area to be catheterized, and the proximal end outside the patient. The catheter or other cannula is introduced into the patient by passing a catheter over the guide wire 21 in accordance with standard medical procedures.

Preferably, the apparatus used in the present method is the advancer 10 or the assembly 12. However, it should be understood, based on this disclosure, that other similar advancing devices having suitable tips and exterior gripping surfaces which are capable of carrying out the steps of the preferred method as described herein and allowing access to the thumb and a finger for controllably advancing the guide wire 21 by feeding may be used.

It will be appreciated by those skilled in the art that changes could be made to the embodiments described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. A guide wire advancer, comprising:
   a. a distal portion having a passageway extending longitudinally therethrough, the distal portion capable of straightening a guide wire;
   b. a proximal portion having a passageway extending longitudinally therethrough; and
   c. a central portion having flexible first and second members extending between the distal portion and the proximal portion, the first and second members defining an opening therebetween, wherein compression of the opening by deformation of the first and second members moves the proximal portion toward the distal portion to advance a guide wire through the passageways.

2. The advancer of claim 1, wherein the distal portion is conical.

3. The advancer of claim 1, wherein an exterior surface of a tip of the distal portion is configured to mate with an interior surface of a guide wire introducer.

4. The advancer of claim 1, wherein the passageway in the distal portion and the passageway in the proximal portion are generally aligned along a longitudinal axis.

5. The advancer of claim 1, wherein the first and the second members are arcuate.

6. A guide wire advancer assembly comprising:
   a. a guide wire advancer including:
      i. distal portion having a passageway extending longitudinally therethrough, the distal portion capable of straightening a guide wire;
      ii. a proximal portion having a passageway extending longitudinally therethrough;
      iii. a central portion having first and second members extending between the distal portion and the proximal portion, the first and second members defining an opening therebetween, wherein compression of the opening by deformation of the first and second members moves the proximal portion toward the distal end portion to advance a guide wire through the passageways; and
   b. a guide wire storage tube configured to mate with the proximal portion.

7. The assembly of claim 6, wherein the distal portion is conical.

8. The assembly of claim 6, wherein an exterior surface of a tip of the distal. portion is configured to mate with an interior surface of a guide wire introducer.

9. The assembly of 6, wherein the passageway in the distal portion and the passageway in the proximal portion are generally aligned along a longitudinal axis.

10. The assembly according to claim 6, wherein the first and the second members are arcuate.

11. The assembly according to claim 6, further comprising a guide wire within the storage tube.

12. A method for advancing a guide wire, the method comprising the steps of:
   a. compressing an opening in an advancer by deforming flexible members of the advancer to move a proximal portion of the advancer toward a distal portion of the advancer to advance the guide wire;
   b. releasing the deformed flexible members to decompress the opening in the advancer, thereby separating the proximal portion of the advancer from the distal portion; and
   c. repeating steps (a) and (b), as necessary, to advance the guide wire a desired distance.

13. The method of claim 12, wherein releasing the deformed flexible members to decompress the opening in the advancer, thereby separating the proximal portion of the advancer from the distal portion, results in no movement of the guide wire.

14. The method of claim 12, further comprising, prior to step (a), the step of mating the distal portion of the advancer into a proximal end of a guide wire introducer.

15. The method of claim 12, wherein the guide wire introducer is a needle having a lumen extending therethrough, wherein the lumen is aligned with a guide wire passageway in the distal portion of the advancer.

16. The method of claim 12, further comprising, prior to step (a), the steps of:
   a. passing the guide wire through a passageway in the proximal portion of the advancer;
   b. passing the guide wire through the opening in the advancer; and
   c. feeding the guide wire into a passageway in the distal portion of the advancer.

17. The method of claim 12, wherein the guide wire is enclosed in a storage tube, and the method further comprises, before step (a), the step of mating the storage tube to the proximal portion of the advancer.

* * * * *